US00PP18415P3

(12) United States Plant Patent
Scully

(10) Patent No.: US PP18,415 P3
(45) Date of Patent: Jan. 15, 2008

(54) ZOYSIAGRASS PLANT NAMED 'BA-305'

(50) Latin Name: ***Zoysia japonica*×*Zoysia tenuifolia***
Varietal Denomination: BA-305

(75) Inventor: Brian T. Scully, Ft. Pierce, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 37 days.

(21) Appl. No.: 11/174,338

(22) Filed: Jul. 5, 2005

(65) Prior Publication Data

US 2007/0022507 P1 Jan. 25, 2007

(51) Int. Cl.
*A01H 5/00* (2006.01)

(52) U.S. Cl. ..... Plt./390

(58) Field of Classification Search ..... Plt./390
See application file for complete search history.

*Primary Examiner*—Kent Bell
*Assistant Examiner*—Anette H Para

(57) ABSTRACT

A newly discovered, and asexually reproduced genotype of Zoysiagrass with a distinct set of foliar, inflorescent and agronomic traits.

6 Drawing Sheets

Genus and species name

This invention relates to a new and distinct genotype of Zoysiagrass derived as the progeny from the $F_1$ variety named 'Emerald', which is an interspecific hybrid between *Zoysia japonica* Stued.×*Zoysia tenuifolia* (L.) Merr. It is described herein as 'BA-305'. As used herein 'BA-305' has the identical meaning as "Pristine Zoysia".

BACKGROUND OF THE INVENTION

This invention was discovered and identified in Palm Beach County, Fla. It was a unique and distinctly different vegetative inclusion growing in a planting of the unpatented Zoysiagrass variety known as 'Emerald'. 'BA-305' is postulated to be either a spontaneous mutation that originated from 'Emerald', or derived as the progeny from an outcross to an unknown pollen parent.

'BA-305' was initially propagated asexually from a single 1.5 inch plug taken from the off type inclusion noted above. Over a five-year period there have been multiple vegetative increases at various research sites throughout Florida, and 'BA-305' has remained uniform and genetically consistent. The denomination of this new invention is 'BA-305', but in commerce 'BA-305' has been tested under the synonym "Pristine Zoysia", which will be its commercial designation in the United States.

The distinctness of 'BA-305' from 'Emerald', its putative progenitor, is based on four sets of traits including:

1) floral morphology;

2) leaf and stem morphology;

3) color and pigmentation; and 4) rate of growth and cover.

Measures of disease and insect resistance yielded no significant statistical differences.

For the purpose of registration under the "International Convention for the Protection of New Varieties of Plants" (generally known by its French acronym UPOV Convention) and noting Sections 1612 of the Manual of Patent Examination Procedures the new variety of Zoysiagrass of the present invention is named 'BA-305'.

BRIEF DESCRIPTION OF DRAWINGS

FIG. 1: A comparative photograph of 'BA-305' (left) and 'Emerald' (right). Both pots were allowed to grow side-by-side, uncut and under identical cultural practices. This photograph illustrates the higher biomass production of 'BA-305' compared to 'Emerald'

FIG. 2: A aerial photograph of 'Emerald' (left) and 'BA-305' (right) illustrates the volume of leaf area produced by 'BA-305'.

Both pots were grown side-by-side, uncut and under the same cultural practices.

FIG. 3: A comparative photograph of 'Emerald' (left) and 'BA-305' (right) grown in trays in Belle Glade, Fla. This photograph illustrates the difference in texture and color between the two genotypes. Both sets of trays were grown side-by-side, uncut, and under identical cultural practices.

FIG. 4: Breeders Block of 'BA-305' growing in Avon Park, Fla.

FIG. 5: A close-up photograph of the freshly cut Breeders Block of 'BA-305'.

FIG. 6: A side profile photograph of 'BA-305' after a recent cutting.

DETAILED DESCRIPTION OF THE VARIETY

This new variety of Zoysiagrass is a perennial plant propagated asexually from either rhizomes, stolons, sprigs, or plugs. It is best adapted to the subtropical climates of Florida. 'BA-305' was tested and described under field conditions at four research sites in Florida, including Arcadia, Belle Glade, Gainesville, and Milton. Phenotypically, 'BA-305' is most similar to 'Emerald' but it has a more refined morphology.

The floral morphology of 'BA-305' is typical of the interspecific hybrid *Zoysia japonica* Stued. by *Zoysia ter-*

*ruifloia* (L.) Merr. as represented by the variety 'Emerald'. 'BA-305' and 'Emerald' were compared to eight inflorescences traits (Table 1) and the two genotypes were significantly different from seven of the eight traits. In each case 'BA-305' had a smaller and more refined morphology. 'BA-305' had a significantly shorter overall shoot length, seed head length, peduncle length and the exposed peduncle length, although shorter, was not statistically significant (Table 1). Seed head width and the average number of seeds per raceme (Seed Count/Seed Head) were also significantly smaller. Additionally, 'Emerald' had a higher seed density on the raceme than 'BA-305' (0.727 seed/mm vs 0.880 seed/mm), but this trait was not visually discernable. Glume length and glume width were also smaller. Essentially, 'BA-305' had smaller and fewer seeds distributed at a lower density on shorter seed heads with smaller peduncles.

The number of seeds heads produced on a monthly basis varied with season. 'BA-305' produced statistically fewer seed heads then 'Emerald' in June, July, December, January, February, and March. Conversely, 'BA-305' produced statistically more seed heads than 'Emerald' in the months of August, September, and October (Table 4). No statistical differences existed between the two genotypes for seed head production in the months of April, May, or November. 'BA-305' produced fewer seed heads than 'Emerald' in the winter and summer, while 'Emerald' produced fewer seed heads in the fall. This phase change generally occurred in the mid-fall and mid-spring.

The morphology of the flag leaf is described by flag leaf length, width, and sheath length. 'BA-305' differed statistically from 'Emerald' for flag leaf length and sheath length. As with the floral morphology these flag leaf traits were finer for 'BA-305' then 'Emerald' (Table 2). No difference existed in flag leaf width. Stolon and leaf morphology of the vegetative tissue was measured on fully expanded leaves at the fifth node below the stolon meristem. Again, 'BA-305' had a more refined texture then 'Emerald'. Leaf length of 'BA-305' was on average 21% shorter and 19% narrower than 'Emerald' (Table 3). This difference is visually represented in FIGS. 1, 2, and 3. The internode morphology of 'BA-305' was larger than 'Emerald' (Table 3). The average internode length of 'BA-305' was measured at 20.92 mm vs 11.37 mm for 'Emerald'. 'BA-305' produced internodes about 85% longer than 'Emerald', however no meaningful difference existed on internode widths (Table 3).

Leaf color and stolon/rhizome pigment also varied between the two genotypes, and was determined by a comparison of fresh leaf and stolon tissue to color panels in the Munsell Color Chart. The adaxial surface of the leaves of 'BA-305' ranged from 7.5GY (4/6 to 5/6) in color. 'Emerald' produced leaves of less intense color and ranged from 5GY (4/6) to 7.5 GY (4/6). The stolons of 'BA-305' produced a pigment that ranged 5RP (3/2), while 'Emerald' produced a lighter pigment which measured 5RP (4/2) on the Munsell Color Chart.

From the initiation of the growth rate experiment, 'BA-305' covered the plots faster and had significantly more cover in each month of the year. 'BA-305' attained 50% coverage in 5.2 months, while it took 'Emerald' 8.0 months; 100% cover was attained in 11.0 months from 'BA-305' and over 13 months for 'Emerald' (Table 5). This significantly faster rate of coverage gave 'BA-305' an important agronomic advantage relative to harvest interval and crop maintenance. The number of stolons and the stolon length were significantly more and longer for 'BA-305' compared to 'Emerald' (Table 5).

TABLE 1

Comparison of floral traits between 'Emerald' and 'BA-305'.

| | 'Emerald' | | 'BA-305' | | |
|---|---|---|---|---|---|
| Trait (in mm) | Mean | ± s.e. | Mean | ± s.e. | LSD α = 0.05 |
| Overall Shoot length[z] | 35.80 | 1.17 | 26.05 | 0.82 | 5.565 |
| Seed Head Length[y] | 11.76 | 0.55 | 9.65 | 0.40 | 1.908 |
| Seed Head Width[x] | 1.53 | 0.07 | 1.21 | 0.06 | 0.187 |
| Seed Count/Seed Head | 16.10 | 0.87 | 10.90 | 0.48 | 3.10 |
| Exposed Peduncle | 12.40 | 0.91 | 7.95 | 0.80 | 4.95 (ns) |
| Peduncle Length[u] | 23.35 | 1.36 | 15.18 | 0.51 | 5.33 |
| Glume Length[t] | 2.66 | 0.06 | 2.43 | 0.08 | 0.19 |
| Glume Width[s] | 0.89 | 0.02 | 0.81 | 0.04 | 0.06 |

[z]Overall shoot length is a measure of the total inflorescence length from the apex of the seed head to the first node on the peduncle subtending the raceme

[y]Seed Head Length is measured from the apex of the seed head to the top of the peduncle on the base of the raceme.

[x]Seed Head Width is measured at the broadest part of the seed head.

[w]Seed Count/Seed Head is the average number of seeds per head or raceme.

[v]Exposure Peduncle Length is the average length of the peduncle not covered by the flag leaf sheath.

[u]Peduncle Length is the average pinnacle length measured from the base of the seedhead to the top of the node.

[t]Glume Length is a measure of the average glume length on the seed located at the mid point along the seedhead.

[s]Glume Width is measured at the widest part of the glume.

TABLE 2

Comparison of flag leaf traits between 'BA-305' and 'Emerald'

| | 'Emerald' | | 'BA-305' | | |
|---|---|---|---|---|---|
| Trait (in mm) | Mean | ± s.e. | Mean | ± s.e. | LSD α ≦ 0.05 |
| Flag Leaf Length[z] | 9.20 | 0.99 | 4.65 | 0.44 | 1.97 |
| Flag Leaf Width[y] | 0.79 | 0.25 | 0.81 | 0.03 | 0.08 (ns) |
| Flag Leaf Sheath[x] | 11.45 | 0.77 | 8.50 | 0.65 | 2.35 |

[z]Flag Leaf Length is measured from the apex of the leaf to the top of the leaf sheath.
[y]Flag Length Width is measeured at the widest part of the flag leaf.
[x]Flag Leaf Sheath is measured from the top node to the base of the flag leaf.

TABLE 3

Comparison of leaf morphology between 'BA-305' and 'Emerald'.

| | 'Emerald' | | 'BA-305' | | |
|---|---|---|---|---|---|
| Trait (in mm) | Mean | ± s.e. | Mean | ± s.e. | LSD α ≦ 0.05 |
| Leaf Length | 60.80 | 2.16 | 68.07 | 2.66 | 8.34 |
| Leaf Width[z] | 1.96 | 0.08 | 1.59 | 0.07 | 0.25 |
| Internode Length | 11.37 | 0.58 | 20.92 | 0.45 | 2.29 |
| Internode Width[y] | 1.33 | 0.06 | 1.35 | 0.06 | 0.18 (ns) |

[z]Leaf Width is measured at the widest part of the leaf.
[y]Internode Width is measured at the widest part of the internode.

TABLE 4

Comparison of the average seed head production between 'BA-305' and 'Emerald' measured on a monthly basis.

| Seed Head[y] | MONTH | | | |
|---|---|---|---|---|
| | APRIL | MAY | JUNE | JULY |
| 'BA-305' | 0 | 0 | 5.00 ± 2.20 | 7.00 ± 3.76 |
| 'Emerald' | 0 | 0 | 29.00 ± 4.14 | 21.75 ± 3.97 |
| | AUGUST | SEPTEMBER | OCTOBER | |
| 'BA-305' | 27.50 ± 5.62 | 57.75 ± 8.74 | 63.75 ± 10.18 | |
| 'Emerald' | 10.50 ± 2.90 | 12.75 ± 9.86 | 4.750 ± 2.43 | |
| | NOVEMBER | DECEMBER | JANUARY | |
| 'BA-305' | 49.00 ± 9.03 | 25.25 ± 8.35 | 15.50 ± 6.20 | |
| 'Emerald' | 47.75 ± 11.41 | 112.50 ± 15.76 | 120.75 ± 13.98 | |
| | FEBRUARY | MARCH | APRIL | |
| 'BA-305' | 5.50 ± 4.52 | 42.25 ± 29.94 | 60.00 ± 17.25 | |
| 'Emerald' | 128.0 ± 14.43 | 103.75 ± 16.9 | 76.25 ± 12.89 | |

[y]Seed head count is measured as mean ± standard error on a 8.0 $cm^2$ plot basis.

TABLE 5

Comparison of average cover, stolon/rhizome number, and stolon/rhizome length between 'BA-305' and 'Emerald' measured on a monthly basis.

| | MONTH | | | |
|---|---|---|---|---|
| | APRIL | MAY | JUNE | JULY |
| Covered[z] | | | | |
| 'BA-305' | 0 | 1.25 ± 1.25 | 10.75 ± 2.39 | 35.00 ± 6.12 |
| 'Emerald' | 0 0 | 11.25 ± 1.25 | 18.75 ± 3.75 | |
| Stolon Number[x] | | | | |
| 'BA-305' | 0 | 0 | 2.25 ± 1.03 | 7.75 ± 0.63 |
| 'Emerald' | 0 | 0 | 0.25 ± 0.25 | 5.25 ± 1.93 |
| Stolon Length[z] | | | | |
| 'BA-305' | 0 | 0 | 1.75 ± 0.63 | 3.25 ± 0.75 |
| 'Emerald' | 0 | 0 | 0.25 ± 0.25 | 1.75 ± 0.48 |
| | AUGUST | SEPTEMBER | OCTOBER | |
| Covered[z] | | | | |
| 'BA-305' | 42.50 ± 3.23 | 48.75 ± 5.54 | 56.25 ± 5.15 | |
| 'Emerald' | 28.75 ± 3.15 | 33.75 ± 3.75 | 42.50 ± 1.44 | |

TABLE 5-continued

Comparison of average cover, stolon/rhizome number, and stolon/rhizome length between 'BA-305' and 'Emerald' measured on a monthly basis.

| | MONTH | | |
|---|---|---|---|
| Stolon Number[x] | | | |
| 'BA-305' | 11.50 ± 0.87 | 11.50 ± 0.87 | 11.25 ± 0.63 |
| 'Emerald' | 5.25 ± 1.60 | 5.25 ± 1.60 | 7.50 ± 0.87 |
| Stolon Length[z] | | | |
| 'BA-305' | 3.50 ± 0.65 | 4.75 ± 0.85 | 6.25 ± 0.63 |
| 'Emerald' | 2.25 ± 0.48 | 3.50 ± 1.19 | 4.00 ± 0.0 |
| | NOVEMBER | DECEMBER | JANUARY |
| Covered[z] | | | |
| 'BA-305' | 60.00 ± 5.77 | 72.50 ± 3.23 | 77.50 ± 4.79 |
| 'Emerald' | 45.0 ± 0.0 | 50.0 ± 7.04 | 52.5 ± 1.44 |
| Stolon Length[z] | | | |
| 'BA-305' | 6.00 ± 0.71 | — | — |
| 'Emerald' | 4.00 ± 0.0 | — | — |
| Stolon Number[x] | | | |
| 'BA-305' | 11.25 ± 0.83 | — | — |
| 'Emerald' | 7.50 ± 0.87 | — | — |
| | FEBRUARY | MARCH | APRIL |
| Covered[z] | | | |
| 'BA-305' | 83.75 ± 5.91 | 100.00 ± 0 | 100.00 ± 0 |
| 'Emerald' | 57.55 ± 1.44 | 78.75 ± 2.39 | 87.5 ± 6.02 |
| Stolon Number[x] | | | |
| 'BA-305' | — | — | — |
| 'Emerald' | — | — | — |
| Stolon Length[z] | | | |
| 'BA-305' | — | — | — |
| 'Emerald' | — | — | — |

[x]Cover is measured as the cumulative percentage of cover over a prescribed plot area.
[y]Stolon Number is a count of stolon/rhizomes radiating from a central plug over a prescribed plot area.
[z]Stolon Length is a number of the average length in cm of the stolons/rhizomes.

What is claimed is:

1. A new and distinct genotype of zoysiagrass plant substantially described and illustrated herein.

* * * * *

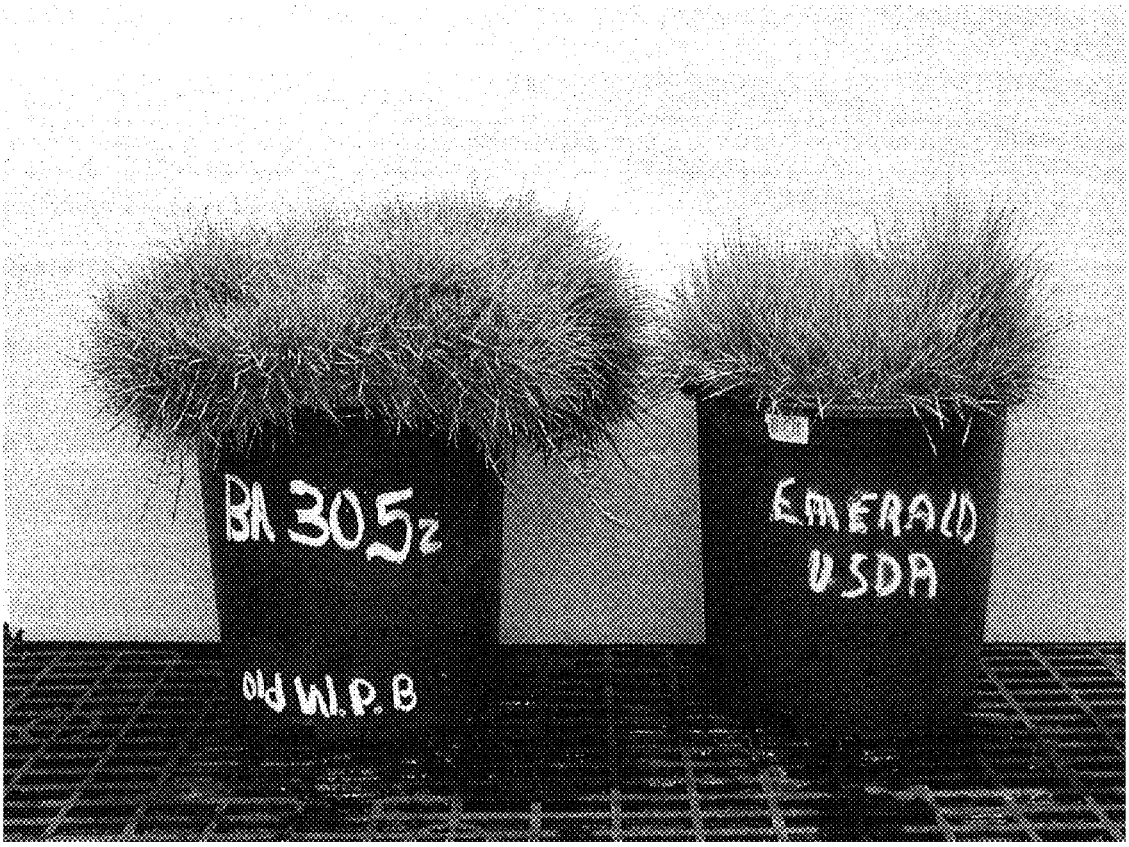
BA 305z
Old W.P.B
EMERALD
USDA

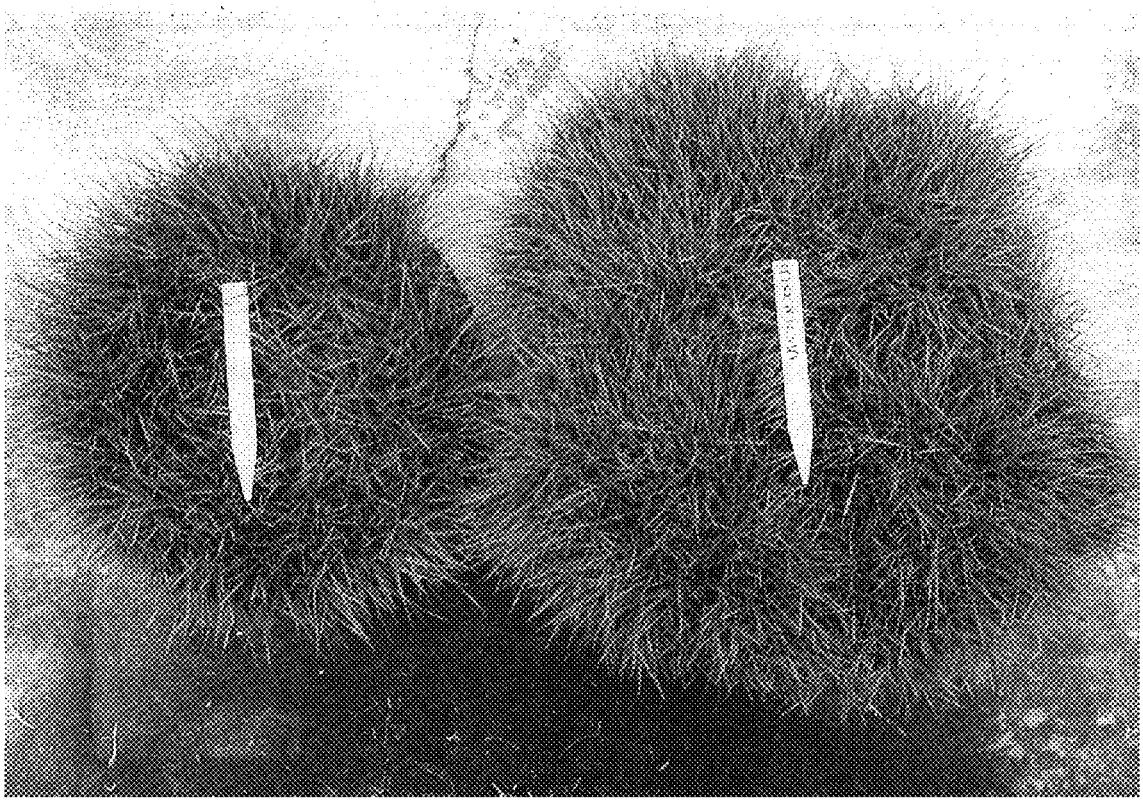

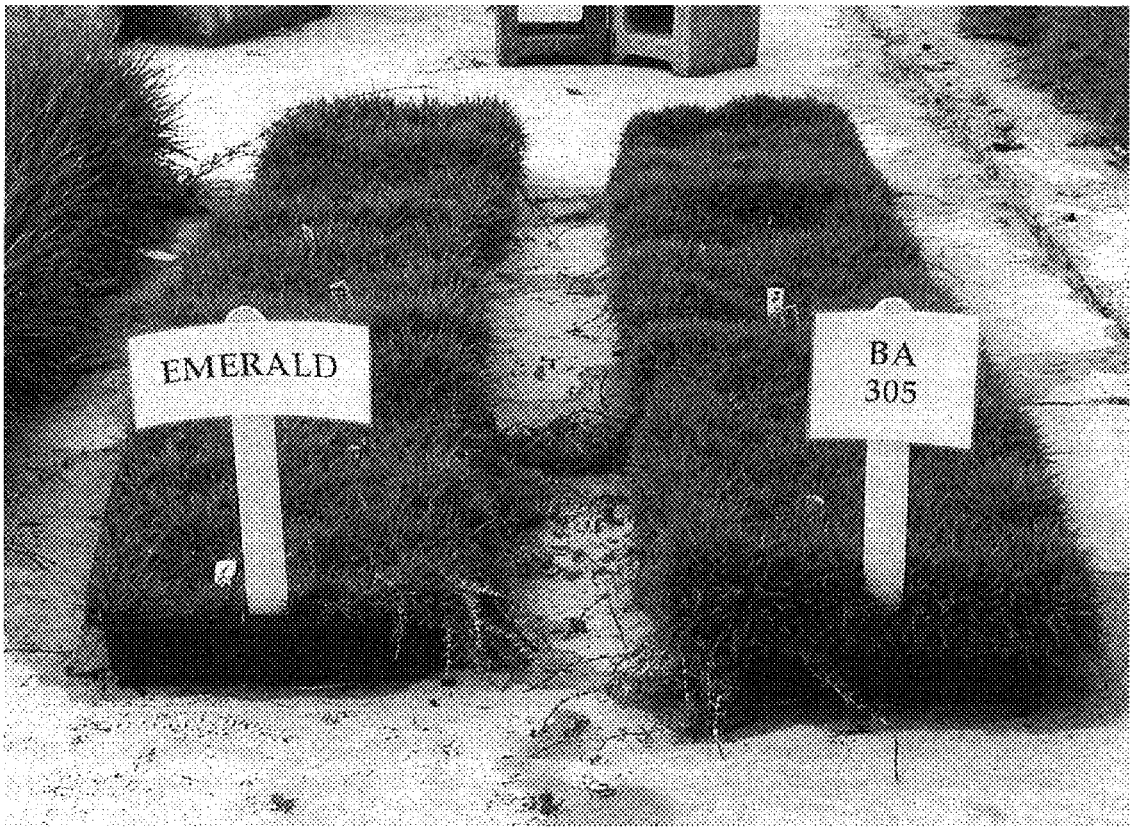
EMERALD
BA
305

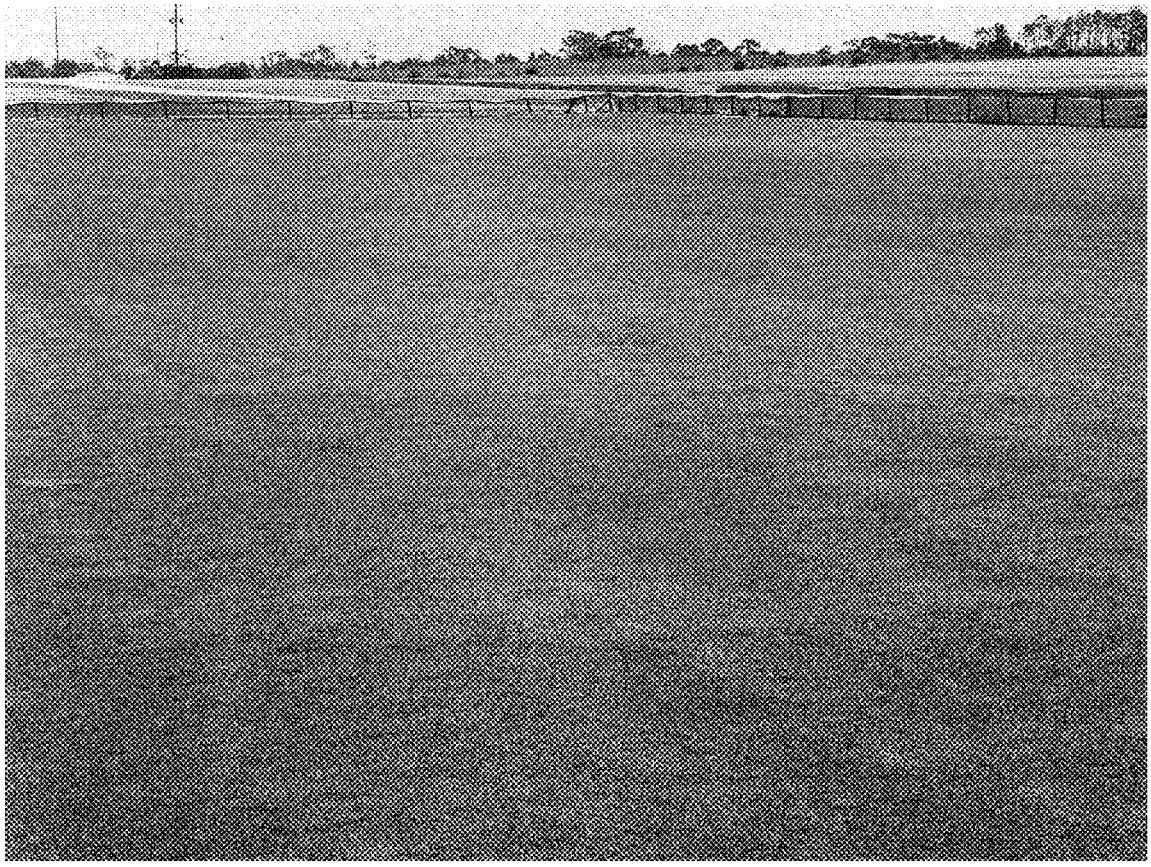

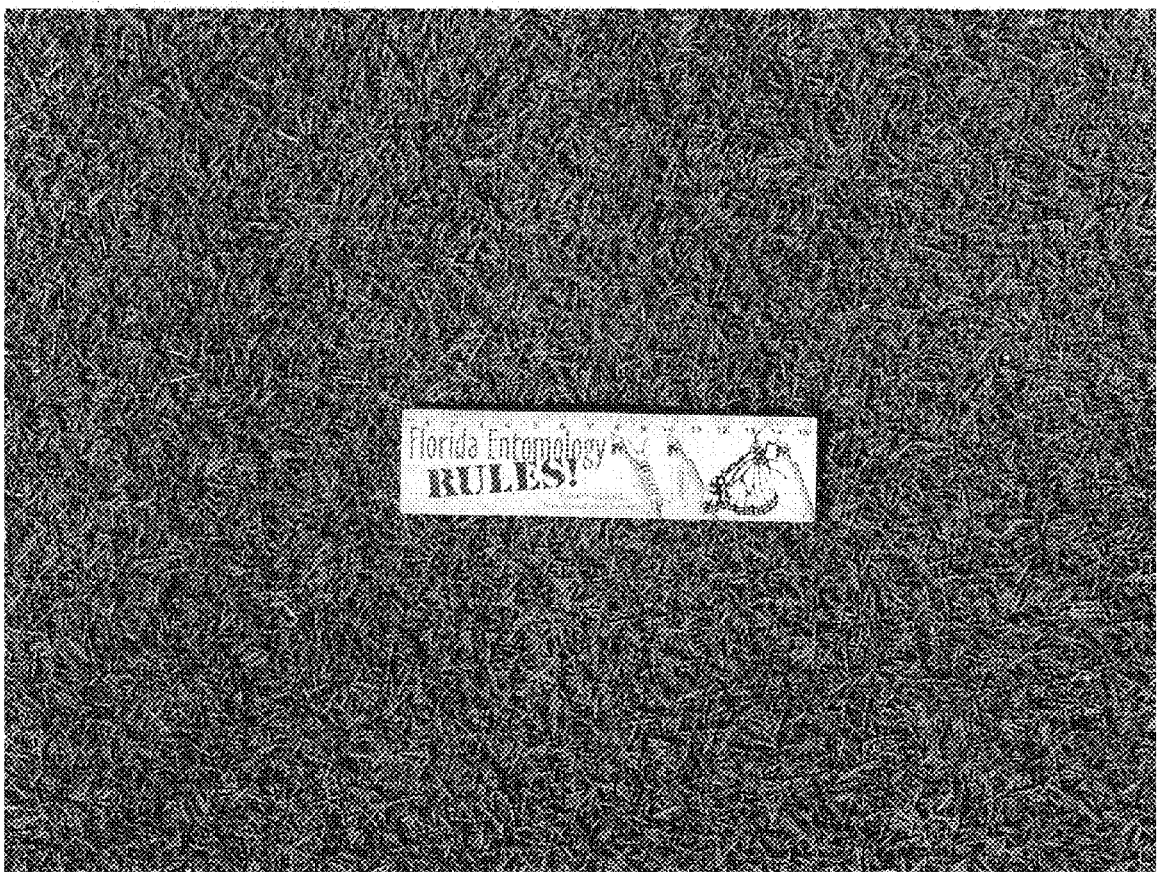
Florida Entomology
RULES!

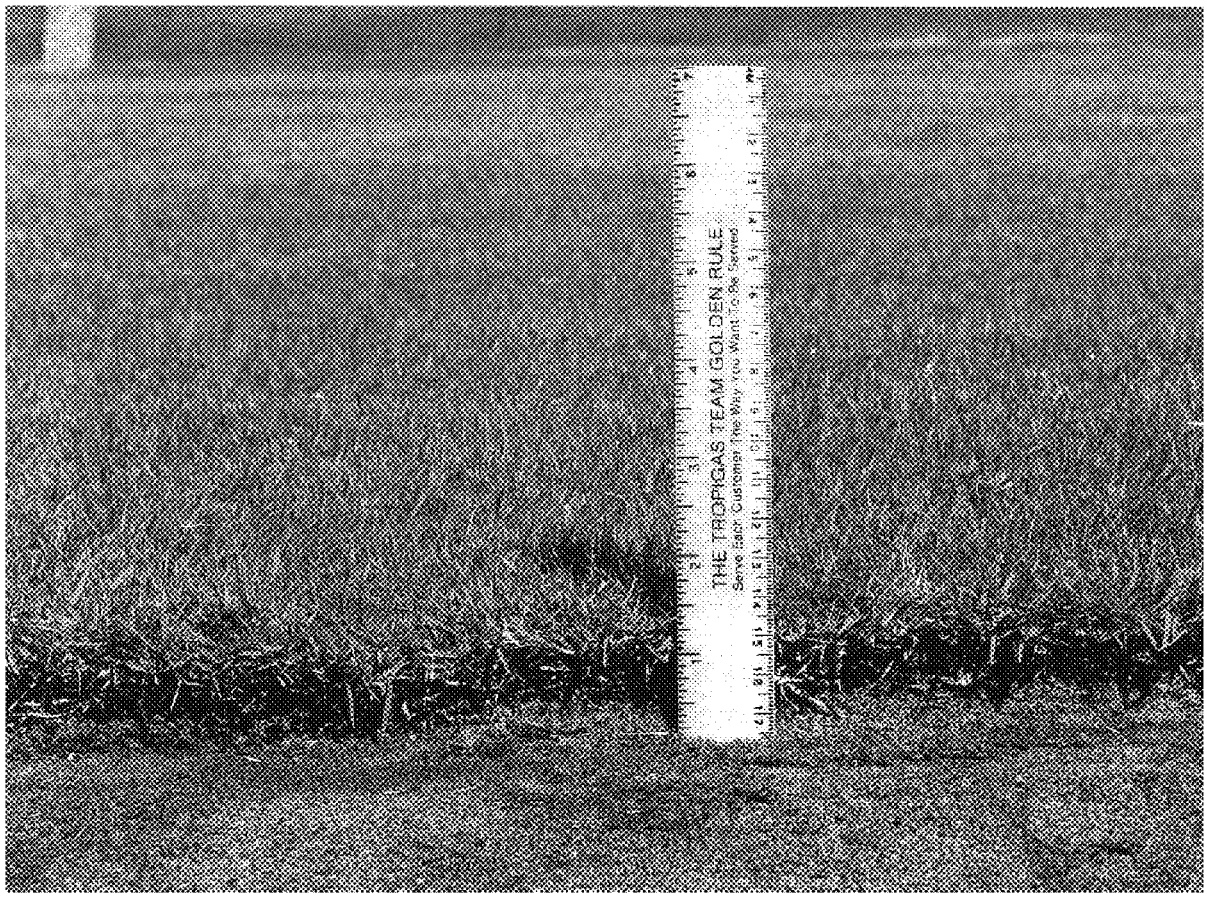
THE TROPICAS TEAM GOLDEN RULE
Serve Each Customer The Way You Want To Be Served